(12) United States Patent
Deliwala et al.

(10) Patent No.: US 9,830,489 B2
(45) Date of Patent: Nov. 28, 2017

(54) SIMPLE CODE READER

(71) Applicant: ANALOG DEVICES, INC., Norwood, MA (US)

(72) Inventors: Shrenik Deliwala, Andover, MA (US); Alain Valentin Guery, Boston, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 0 days.

(21) Appl. No.: 15/094,445

(22) Filed: Apr. 8, 2016

(65) Prior Publication Data

US 2017/0286733 A1 Oct. 5, 2017

Related U.S. Application Data

(60) Provisional application No. 62/314,565, filed on Mar. 29, 2016.

(51) Int. Cl.
| | |
|---|---|
| *G06K 7/10* | (2006.01) |
| *G06K 7/14* | (2006.01) |
| *G06K 19/06* | (2006.01) |
| *G01N 33/66* | (2006.01) |

(52) U.S. Cl.
CPC ......... *G06K 7/10732* (2013.01); *G01N 33/66* (2013.01); *G06K 7/10821* (2013.01); *G06K 7/1404* (2013.01); *G06K 19/06018* (2013.01); *G06K 19/06037* (2013.01)

(58) Field of Classification Search
USPC .......... 235/462.32, 462.01, 462.42; 356/138; 345/156
See application file for complete search history.

(56) References Cited

U.S. PATENT DOCUMENTS

| | | | |
|---|---|---|---|
| 4,683,467 A | * | 7/1987 | Macaulay ................ H04N 3/22 345/207 |
| 6,094,289 A | | 7/2000 | Moranski et al. |
| 7,135,673 B2 | | 11/2006 | Saint Clair |
| 7,474,390 B2 | | 1/2009 | Robinson et al. |

(Continued)

OTHER PUBLICATIONS

ISR-WO issued in International Patent Application Serial No. PCT/US2017/021630 dated Jun. 19, 2017, 8 pages.

*Primary Examiner* — Allyson Trail
(74) *Attorney, Agent, or Firm* — Patent Capital Group (57) ABSTRACT

Embodiments of the present disclosure provide code readers for reading codes provided as patterns imprinted on objects. Light interacts with a pattern by e.g. being reflected from or transmitted through the pattern, and at least some of the light that has interacted with the pattern is incident on photosensitive element(s) of one or more photodetectors of a code reader. The code reader employs centroid-measuring photodetector(s), i.e. photodetectors that detect light in such a manner that centroid of a pattern can be obtained directly from the photocurrents generated as a result of the photosensitive elements detecting light incident thereon. The code reader is then configured to process the detected light to determine a centroid of the pattern from the detected light and to decode data encoded in the pattern based on a position of the centroid. Such code readers are substantially less complex than camera-based devices and avoid mechanical scanning.

20 Claims, 7 Drawing Sheets

(56) References Cited

U.S. PATENT DOCUMENTS

| | | |
|---|---|---|
| 7,522,190 B2 | 4/2009 | Inada |
| 7,710,553 B2 | 5/2010 | Hollander |
| 7,729,515 B2 | 6/2010 | Mandella et al. |
| 8,274,586 B2 | 9/2012 | Katsuno et al. |
| 9,201,000 B2 | 12/2015 | Kiesel et al. |
| 2010/0315461 A1* | 12/2010 | Mongeon ............... B41J 29/393 347/19 |
| 2012/0262365 A1* | 10/2012 | Mallinson ............... G01S 1/725 345/156 |
| 2013/0155396 A1* | 6/2013 | Deliwala ............... G01J 1/0242 356/138 |
| 2014/0368618 A1 | 12/2014 | Ushinaga et al. |
| 2016/0353070 A1* | 12/2016 | Okamoto ........... H05B 33/0869 |

\* cited by examiner

SIMPLE CODE READER

CROSS-REFERENCE TO RELATED APPLICATIONS

This application claims the benefit of and priority from U.S. Provisional Patent Application Ser. No. 62/314,565 filed 29 Mar. 2016 entitled "SIMPLE CODE READER," which is incorporated herein by reference in its entirety.

TECHNICAL FIELD OF THE DISCLOSURE

The present invention relates to the field of optical detectors, in particular to systems and methods for reading data embedded in imprinted patterns.

BACKGROUND

Many forms of readers that read data embedded in printed patterns exist. Data embedded in a spatially varying pattern is generally referred to as a "code" or as "encoded data" and a reader for decoding the data from the pattern is referred to as a "code reader."

Existing code readers typically use either a camera or a scanning light beam to read the encoded data. For example, scanners used at the check-out in grocery stores are examples of code readers using scanning light beams. Line scanners (also sometimes referred to as "one-dimensional cameras") are another example of code readers, in which an object with a pattern printed thereon and a line camera are moved past each other, as is done e.g. in fax machines or flat-bed scanners. Two-dimensional (2-D) camera based systems provide yet another example of code readers, where a 2-D camera acquires the image and then processes it to determine the data encoded therein.

All of these code readers are relatively expensive systems that require many pixels, substantial image processing capabilities, or/and assemblies that include mechanically moving parts that are prone to breaking. In addition, code readers using cameras and line scanners are sensitive to ambient light conditions and object placement and require careful selection of optics, e.g. focusing elements, and electronics processing. While code readers such as laser scanners may be more tolerant to ambient light and may function without focusing, they use cumbersome mechanical assemblies.

For the reasons described above, including existing code readers in e.g. consumer electronic devices or medical assemblies that may require reading of codes is often not technically possible, has prohibitively high complexity, and/or is simply too expensive. In particular, as modern electronics are becoming more and more ubiquitous in healthcare, medical equipment is often provided with electronic components and algorithms to sense, measure, and monitor living beings. For example, diabetes is a lifelong disease affecting glucose levels in millions of people across the world, often with dire consequences. Modern electronics enable managing this disease by providing glucose measuring devices (generally referred to as "glucose meters") to people with diabetes. A diabetic person can put a drop of his or her blood on a glucose metering strip, insert the strip with the blood into the glucose meter, and find out a glucose level based on the tests that the glucose meter performs on the blood in the strip. In order for a glucose meter to perform its measurements correctly, the meter often needs information regarding the glucose strip, such as e.g. the nature and amounts of chemical compounds included in a particular strip. It would be desirable to be able to encode this information into a code that can be provided on a strip and to be able to supply every glucose meter with a code reader that can decode the information from such codes on the strips. In this context, as well as with other medical device assemblies, consumer electronics, or electronics in general, low cost and simplicity of a code reader is critical for its viability in the marketplace.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Embodiments of the present disclosure provide code readers that are substantially less complex than camera-based devices, avoid mechanical scanning, and do not require cumbersome mechanical assemblies. Code readers described herein may be used in any systems that require decoding data encoded into spatially varying patterns imprinted on an object, and may be especially attractive for medical device assemblies such as, but not limited to, glucose meter and glucose metering strip assemblies, medicine dispenser and medicine container assemblies (e.g. diffusion pumps into which medicine-containing tubes are inserted), or for consumer electronic applications.

One aspect of the present disclose provides a medical device assembly comprising: a medical device reader configured to perform measurements on a medical device object, the medical device reader comprising a code reader, and the medical device object configured to be affixed to, aligned with, or inserted into the medical device reader and having a code provided thereon as a pattern imprinted on the object. The code reader comprises one or more centroid-measuring photodetectors configured to, when the medical device object is affixed to, aligned with, or inserted into the medical device reader, detect light that has interacted with the pattern, wherein the detected light is indicative of a centroid of the pattern; and a processing logic configured to determine the centroid of the pattern from the detected light, and determine the code based on the determined centroid (i.e., decode the data encoded in the pattern provided on the object).

Another aspect of the present disclose provides a code reading system comprising a first centroid-measuring photodetector configured to detect light that has interacted with a first pattern provided on an object, wherein the first pattern encode data (i.e. the first pattern represent a code encoding data) and wherein the detected light is indicative of a centroid of the first pattern; and a processing logic configured to determine the centroid of the first pattern from the detected light, and decode the data encoded in the first pattern based on the determined centroids of the first pattern.

As will be appreciated by one skilled in the art, aspects of the present disclosure may be embodied in various manners—e.g. as a method, a system, a computer program product, or a computer-readable storage medium. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Functions described in this disclosure may be implemented as an algorithm executed by one or more processing units, e.g. one or more microprocessors, of one or more computers. In various embodiments, different steps and portions of the steps of each of the examples described herein may be performed by different processing units. Furthermore, aspects of the present disclosure may take the form of a computer program product embodied in one or more computer readable medium(s), preferably non-transitory, having computer readable program code embodied, e.g., stored, thereon. In various embodiments, such a computer program may, for example, be downloaded (updated) to the existing devices and systems or be stored upon manufacturing of these devices and systems.

Other features and advantages of the disclosure are apparent from the following description, and from the claims.

Embodiments of the present disclosure provide code readers for reading codes provided as patterns imprinted on objects. As used herein, the term "code" refers to a pattern, provided on an object, the pattern representing (i.e. encoding) certain data to be conveyed. A pattern may e.g. be imprinted on an object, where the term "imprinted" encompasses patterns printed, stamped, punched, impressed, engraved, debossed, etched, or marked on an object in any other manner. "Imprinted" also include patterns provides as openings or holes in an object, e.g. by being punched through. Light interacts with a pattern (e.g. is reflected from the pattern, is transmitted through the pattern, is partially absorbed by the pattern, etc.) and at least some of the light that has interacted with the pattern is incident on the photosensitive elements of one or more photodetectors of one of the code readers described herein. In particular, embodiments of the present disclosure provide code readers that use centroid-measuring photodetectors, i.e. photodetectors that detect light in such a manner that centroid of a pattern can be obtained directly from the photocurrents generated as a result of the photosensitive elements of the photodetectors detecting light incident thereon. The code reader is then configured to process the detected light to determine a centroid of the pattern from the detected light and to decode the data encoded in the pattern based on a position of the centroid. As a result, code readers that are substantially less complex than camera-based devices and avoid mechanical scanning may be obtained.

Figure 1A:
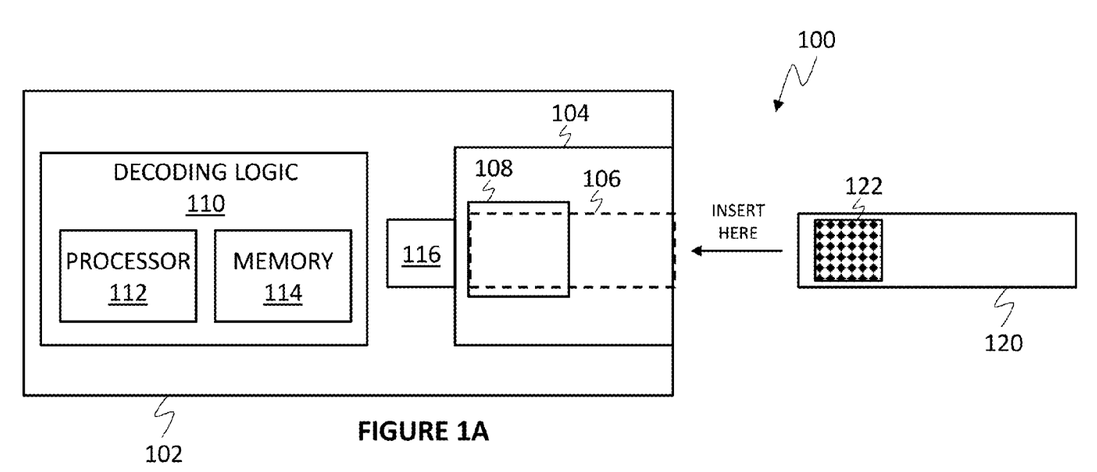
FIGS. 1A and 1B depict block diagrams illustrating an exemplary code reading assembly of a code reader and an object with a pattern imprinted thereon, according to some embodiments of the disclosure.
Figure 1B:
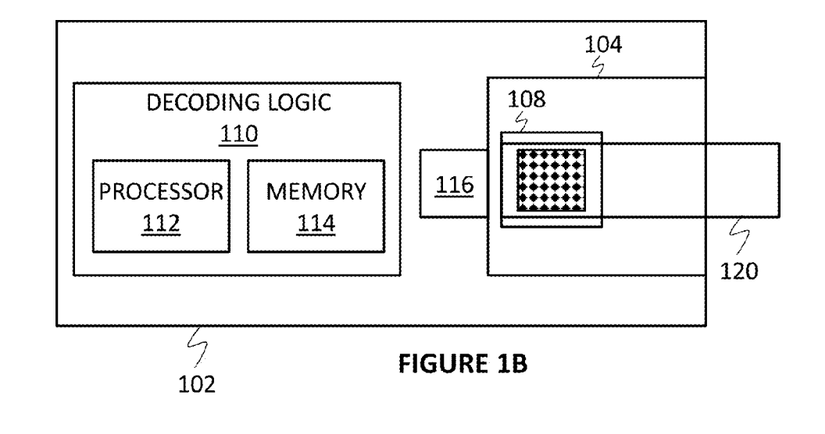
Figure 6:
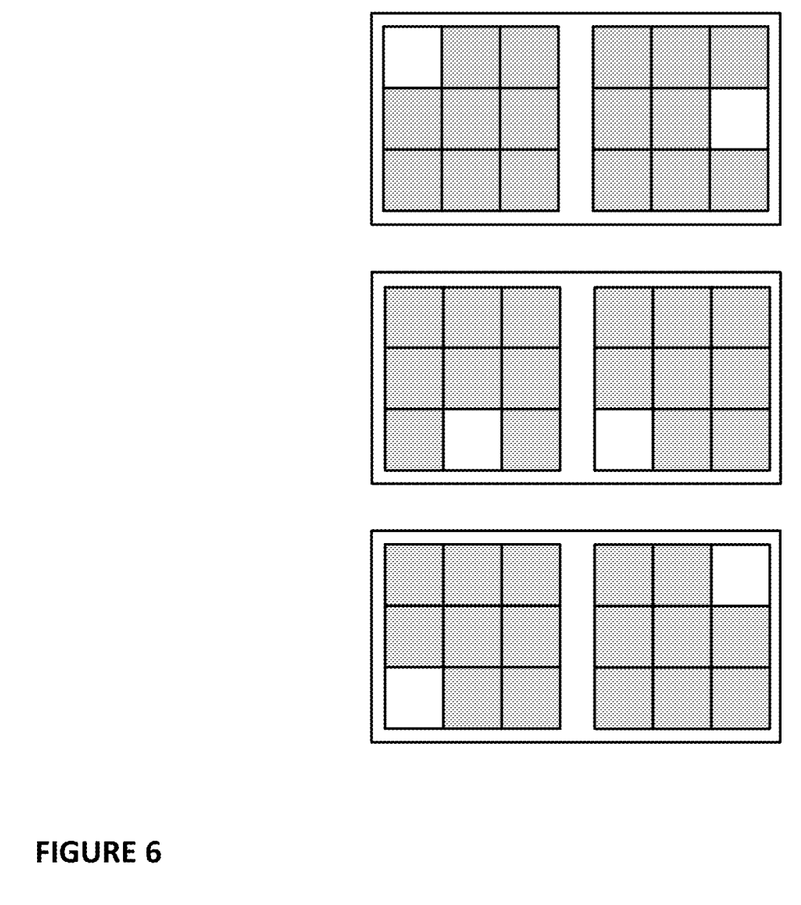
FIG. 6 illustrates examples of differential patterns that could be read using one of the differential code readers described herein, according to some embodiments of the disclosure.

FIGS. 1A and 1B depict block diagrams illustrating an exemplary code reading assembly 100 of a code reader 102 and an object 120 with a pattern 122 imprinted thereon, according to some embodiments of the disclosure. Various embodiments of the present disclosure are by no means limited to the patterns as illustrated in the FIGUREs as examples, such as e.g. the pattern 122 or patterns shown in FIGS. 3 and 6.

In some embodiments, the code reader 102 and the object 120 form an assembly, e.g. an assembly used as a medical device, in the object 120 could be a glucose meter strip and the code reader 102 could be or could be included within a glucose metering device.

The code reader 102 is configured to read the code of the pattern 122. To that end, the code reader 102 includes a portion 104, which could be referred to as a connector for the object 120 to the code reader 102, that includes one or more centroid-measuring photodetectors 108 configured to detect light that has interacted with the pattern 122. In some embodiments, the code reader 102 may also include one or more light sources 116 for generating light that then interacts with the pattern 122, e.g. by being coupled into a waveguide configured to illuminated the pattern 122, by being reflected on the pattern 122, by being transmitted through the pattern 122, and/or by being partially absorbed by the pattern 122.

In various embodiments, the light source 116 may comprise a light emitting diode (LED), or any suitable component for emitting light. The light emitted by the light source 116 can be of any suitable wavelength (or a range of wavelengths), depending on the application.

In other embodiments, the code reader 102 does not include any additional light sources used for reading of codes, such as the light source 116, and instead ambient light may be used to interact with the pattern 122 and to be detected by the photodetectors 108. For example, the pattern 122 may be provided in the object 120 so that it is inserted in the object in such a way that light incident on one side (one surface) of the pattern can be at least partially transmitted through the pattern, emerging from the other side of the pattern. Thus, the object 120 would serve as a frame, framing the pattern 122. Such a pattern could then be aligned with the code reader 102 in such a way that ambient light is incident on one surface of the pattern, and the photodetectors 108 provided on the other side of the pattern detect portion of the incident ambient light that has been transmitted through the pattern.

The code reader 102 is configured to read the code of the pattern 122, and possibly perform other measurements on the object 120, such as e.g. glucose level reading, when the object 120 is affixed to, aligned with, or inserted into the code reader 102 so that the centroid-measuring photodetectors 108 could determine the centroid of the pattern 122. FIG. 1A illustrates a scenario where the object 120 is not yet inserted into the code reader 102, where dashed box 106 indicates position of the object 120 once it is inserted into the code reader 102, while FIG. 1B illustrates a scenario after the insertion of the object 120 into the core reader 102. While FIG. 1A indicates direction of insertion of the object 120, descriptions provided herein are not suitable to the object being inserted into the code reader and are applicable to any suitable alignment between the pattern 122 comprising the code to be read and the one or more centroid-measuring photodetectors 108 of the code reader 102 that would allow the photodetectors to determine the centroid of the pattern. For example, the object 120 could be clapped onto the code reader 102 or affixed to the code reader in any other manner. Specific issues related to alignment are described in greater detail below.

As also illustrated in FIG. 1, the code reader 102 include processing logic, shown as decoding logic 110, configured to determine the centroid of the pattern 122 from the detected light and to determine the code of the pattern based on the determined centroid (i.e., decode the data encoded in the pattern provided on the object 120), in accordance with the code reading techniques described herein. To that end, in some embodiments, the decoding logic 110 may include at least a processor 112 and a memory 114, as shown in FIG. 1, configured to implement and/or control various light detection and code reading techniques described herein.

While FIG. 1 illustrates the decoding logic 110 to be included within the code reader 102, in other embodiments, the decoding logic 110 may be implemented external to the code reader 102, in which case the decoding logic 110 may be configured to exchange data with the code reader 102, in particular exchange data with the photodetectors 108 and e.g. control the light source(s) 116, remotely, via any appropriate communication channel. In other words, instead of being implemented within the code reader 102 as shown in FIG. 1, the decoding logic 110 may be external to the code reader 102 and be communicatively coupled to the code reader 102.

Light falling on a photodetector surface can have a non-uniform pattern of light such as when a lens is used to create an image of an outside world on a surface of a photodetector such as camera. Light falling on a surface can also have non-uniform angular distribution if the light is incident on the photodetector from different directions emanating from different objects. As is well-known, a lens "converts" the angular distribution of incident light rays to spatial distribution of intensity on the focal plane. In some embodiments, a lens may be used to converge the light that has interacted with the pattern 122 onto the photodetectors 108.

In various embodiments of the present disclosure, three different kinds of centroid-measuring photodetectors may be used.

One kind of a centroid-measuring photodetector is a lateral photodiode that measures the centroid of the spatial distribution of light on its surface. This requires that a lens be placed between the pattern 122 and the plane of the photodetector 108 to form the spatial distribution as in any camera. A lateral photodiode includes a charge-generating region at least partially enclosed between at least two, but possibly more (for example four), charge-collecting electrodes. The charge-generating region is configured to generate charge as a result of the light being incident on the region, in this case, the light that has interacted with the pattern 122, and the amount of charge collected at each of the charge-collecting electrodes (in particular, the difference between the amounts of charge collected at each electrode) is indicative of the centroid of the pattern.

Figure 2:
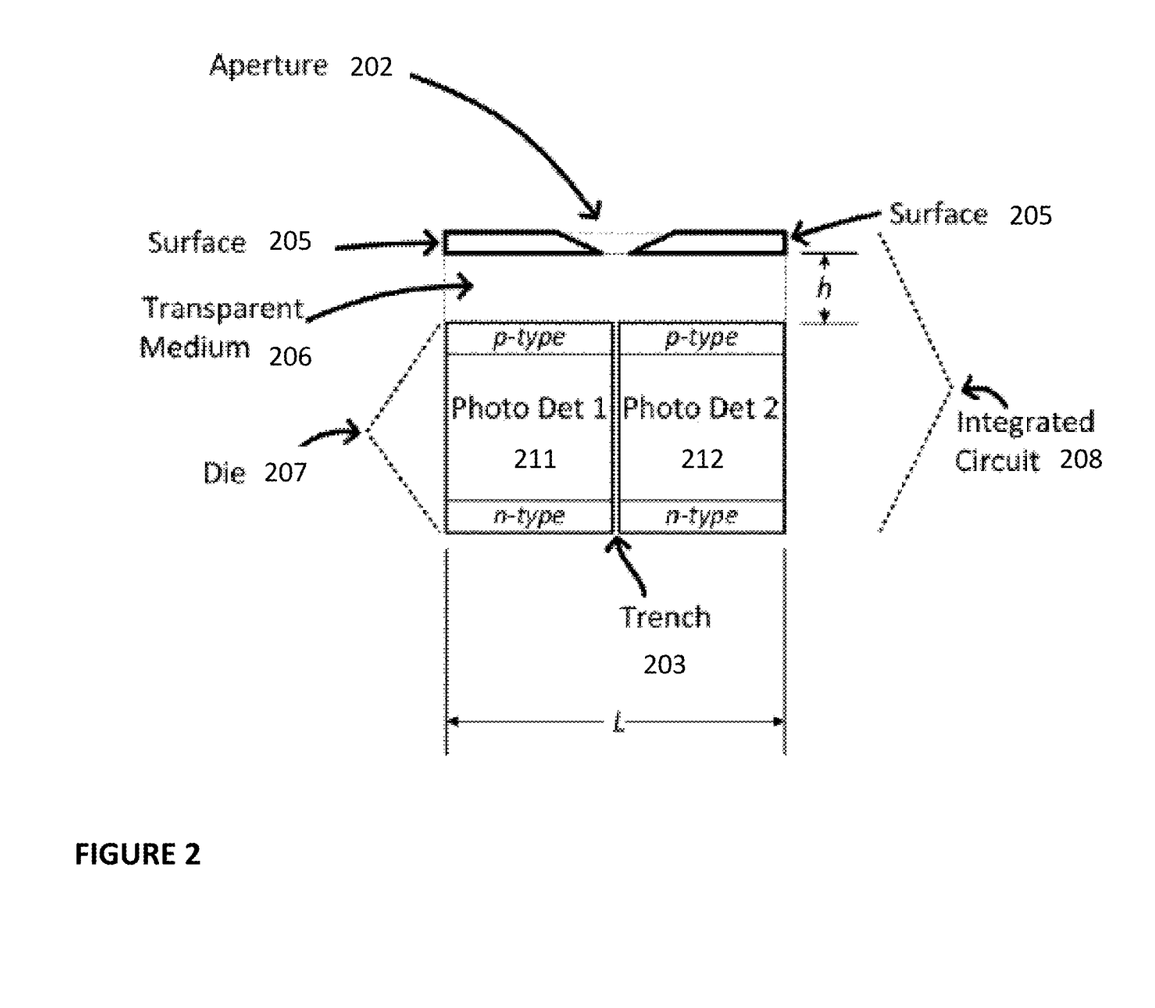
FIG. 2 illustrates an example of an angle sensor, according to some embodiments of the disclosure.

Another kind of a centroid-measuring photodetector may be referred to as an "angle sensor" because it is based on the direct measurement of the incident angular distribution of the light (again, the light that has interacted with the pattern 122). Such a photodetector is described in US patent application US2013/0155396, assigned to the same Assignee as the present application, the disclosure of which is incorporated herein in its entirety. FIG. 2 illustrates an exemplary side-view perspective of such an angle sensor 200, according to some embodiments of the disclosure.

As shown in FIG. 2, the photodetector 200 includes a surface 205 having an aperture 202 and a pair of photodetectors 211 and 212 electrically isolated from each other at a boundary between them, the boundary aligned with the aperture. In the example of FIG. 2, the boundary providing electrical isolation of the pair of photodetectors is shown as a trench 203. However, other ways to provide such a boundary are within the scope of the present disclosure. Light that has interacted with the pattern 122 may be incident on the surface 205 and pass through the aperture 202 to reach the photodetectors 211 and 212. It should be noted that while FIG. 2 illustrates a single photodetector 200 with a pair of sub-photodetectors 211 and 212, and a single aperture 202, in different embodiments, different numbers of apertures and photodetectors may be used.

The apertures 202 may be slits having a width s, and the aperture 202 may be positioned at a height h above the photodetectors 211 and 212. In some configurations, h may be less than 30 µm and in some space saving configurations, h may be less than 10 µm or even less than 1 µm. A medium that enables light to pass through it may be placed between one or more apertures 202 and the photodetectors 211 and 212, shown in FIG. 2 as a transparent medium 206. In some instances, the medium may be glass, including forms of glass used during semiconductor device fabrication. The width of the photodetector may depend on an angular range requirement and h.

Each of the pair of photodetectors 211 and 212 is configured to generate a respective photocurrent when light that has interacted with the pattern 122 is incident on the photodetectors, provided that the light is able to reach these two photodetectors 211 and 212. The angle of the light that has interacted with the pattern 122 may be calculated by measuring a relative proportion of photocurrents detected at each of the photodetectors 211 and 212. If the light is angularly distributed so that the light reaches the photodetectors 211 and 212 from multiple angles $\theta$ with intensity $In(\theta)$, as could be the case when the light has interacted with the pattern 122, then the average angular position of the light may be calculated based on the photocurrents generated by each of the sub-photodetectors 211 and 212. From that position, centroid of the pattern 122 may be determined. In other words, such a pair of photodetectors is sufficient to detect the angle of incident light and from that measure the centroid of the pattern, the angle of incident light being detectable based on a ratio of the photocurrents generated respectively by the pair of photodetectors. The pair of sub-photodetectors 211 and 212 is aligned along an optical path without a lens, the optical path leading through the aperture 202 and the photodetectors 211, 212.

In both kinds of photodetectors described above, the centroid is measured in an analog fashion in the sense that the photocurrents generated by two electrodes for a one dimensional measurement and four electrodes for a full two-dimensional measurement directly yield centroid of the image in case of lateral photodiode and of the angular distribution in case of angle sensor. These kinds of photodetectors cannot produce a detailed light distribution that is routinely measured by conventional cameras that include thousands or even millions of photodetectors. However, this is not needed because the photodetectors only need to be able to determine the centroid of the pattern. The decoding logic 110 can be configured to perform simple algebra on the photocurrents measured at the electrodes of the photodetectors 108 to directly obtain an instant value of a centroid of a light distribution of light incident on the photodetectors 108. In the context of the present disclosure, centroid of an image or an angular distribution may be viewed as simply the weighted mean coordinate of the light distribution, similar to e.g. a center-of-mass.

Yet another kind of a centroid-measuring photodetector is a multi-pixel sensor similar to a one-dimensional or two-dimensional camera, configured to directly measure the centroid by integrated electronics that process the data from the pixels. Such sensors are known in the art as used for tracking objects and, therefore, are not described here in detail.

Figure 3:
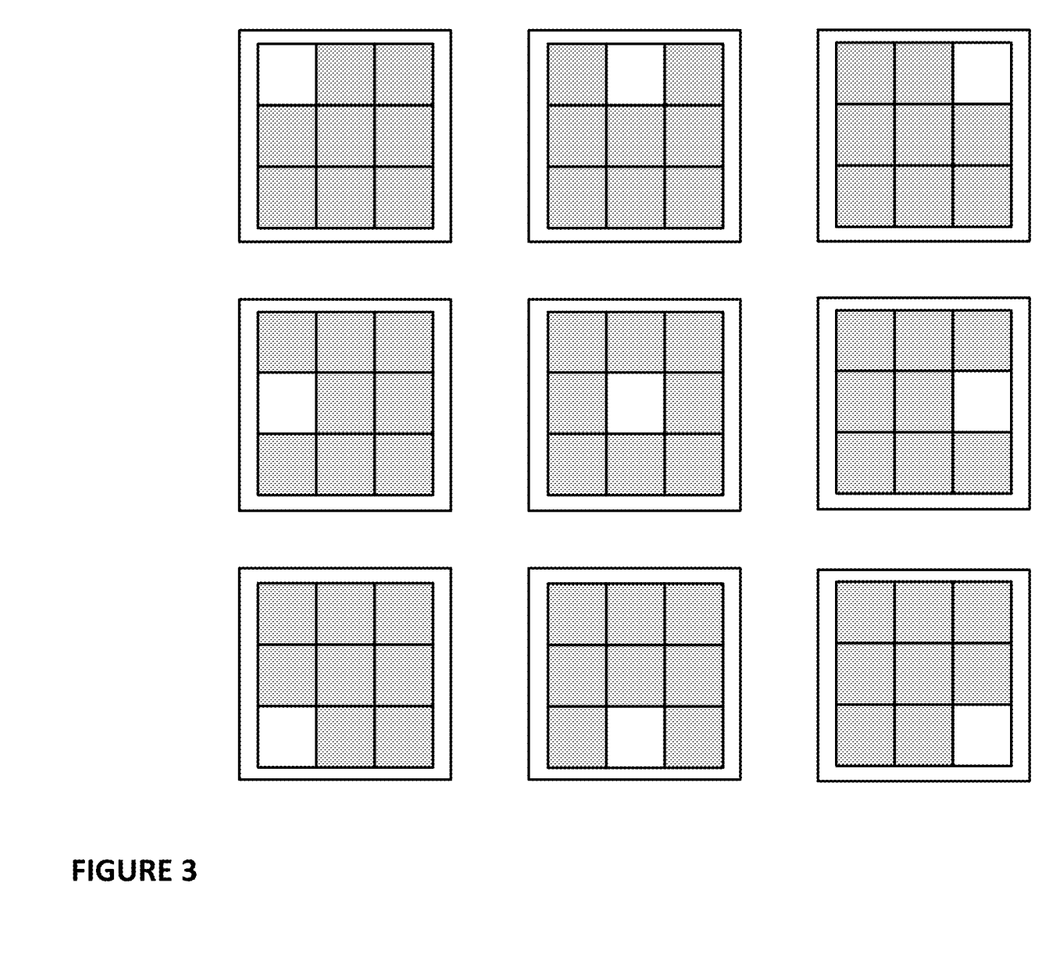
FIG. 3 illustrates examples of patterns that could be read using one of the code readers described herein, according to some embodiments of the disclosure.

In various embodiments, information may be conveyed using simple patterns such as the 8 patterns shown in FIG. 3, each of which could be used as the pattern 122 to be imprinted on the object 120. Patterns shown in FIG. 3 have 9 blocks arranged in a 3×3 grid where one of them is shown as white and others are shown as shaded. The white block represents difference in the pattern with respect to the shaded blocks. For example, if the pattern is a pattern of openings, the white blocks could be the openings in an otherwise continuous surface. In another example, if the code reader uses light reflected from the pattern to read codes, then the white blocks could have reflectivity different from that of the shaded blocks. In yet another example, if the code reader uses light transmitted from the pattern to read codes, then the white blocks could have different transmission/absorption coefficient than the shaded blocks. As would be apparent to a person of ordinary skill in the art based on the descriptions provided herein, any other arrangements are possible, depending on a particular code reader design, all of which are within the scope of the present disclosure.

Patterns of a 3×3 grid as shown in FIG. 3 could be used to encode data corresponding to 9 different codes. Thus, in the view of the photodetector 108 is restricted to within the bounding box surrounding the 3×3 grid, then the centroid-measuring photodetector 108 will yield 9 different (x,y) coordinates for the 9 patterns shown in FIG. 3. Such coding approach could be sufficient in applications such as e.g. medical device assemblies or consumer electronics, where a code reader just needs to read a code that indicates one of a few possible data sets. For example, printing codes such as shown in FIG. 3 on a back of a printed circuit board (PCB) of a glucose metering strip can be easily achievable, at very low cost.

In other embodiments, the patterns may be even simpler than those shown in FIG. 3 in that, e.g. a pattern may simply be a one-dimensional (1-D) pattern. Such patterns could be advantageous because they could make the code reader less sensitive to alignment in one direction and simplify construction of centroid-measuring photodetectors, and could be particularly applicable to deployments where only fewer bits of information need to be coded.

In practical situations, the number of unique coordinate pairs (i.e. the x and y coordinates) of a centroid that can be encoded by position placement of a white block may depend on four primary system parameters: 1) signal to noise ratio (SNR) of the photodetector 108, 2) alignment repeatability between pattern 122 and the photodetector 108, 3) resolution and variability of imprinting the patter 122 on the object 120 (e.g. if done by simple printing of the pattern, then printer resolution and variability), and 4) variability in spatial control of light illumination for the light that interacts with the pattern 122 and is detected by the photodetector 108.

The last parameter, i.e. variability in spatial control of light illumination, can be minimized or eliminated by use of suitable diffusers. Advantageously, none of the centroid-measuring photodetectors described herein depend on absolute light level to report the centroid. Therefore, only the spatial variations in the light illumination are material and those could be reduced or eliminated by providing a suitable diffusing element, e.g. by placing a diffusing element in front of the light source to spread the illumination evenly.

The first parameter, i.e. SNR of the sensor system, can also be addressed relatively easy—e.g. illumination level may be controlled to ensure high SNR. For each of the centroid-measuring photodetectors described above the relative error $\delta x$ or $\delta y$ is proportional to 1/SNR. Thus for a SNR of 1000, or 60 dB, $10^3 \times 10^3$ or million positions can be coded.

The foregoing illustrates that, in a practical situation, it is alignment repeatability (the second parameter) or printer repeatability (the third parameter) that would be the main contributors to determining the number of effective codes that may be encoded for reading using code readers described herein. More or less patterns can be accommodated depending on what is considered to be an acceptable error rate.

The actual angular position may depend on the relative distance between the photodetector 108 and the pattern 122. This can be remedied by using two centroid-measuring photodetectors with overlapping field of view separated by some known distance. Photocurrents measured by such a pair of photodetectors would allow one to deduce the distance between the photodetector 108 and the pattern 122 from simple trigonometry, and the distance could be used to adjust determination of the centroid. This follows from the fact that each of the sensors will measure a different location of the centroid due to its position relative to the pattern. There is only one distance to the pattern from the sensors that will satisfy the relative difference in the angular position measured by the two sensors. This means the distance to the pattern can be determined, which distance can vary depending on a particular setting in which the code reader is deployed, and hence the measured angular position can be corrected for the determined distance. In various embodiments this may be carried out via e.g. trigonometric calculations or by using a look-up table.

Figure 4A:
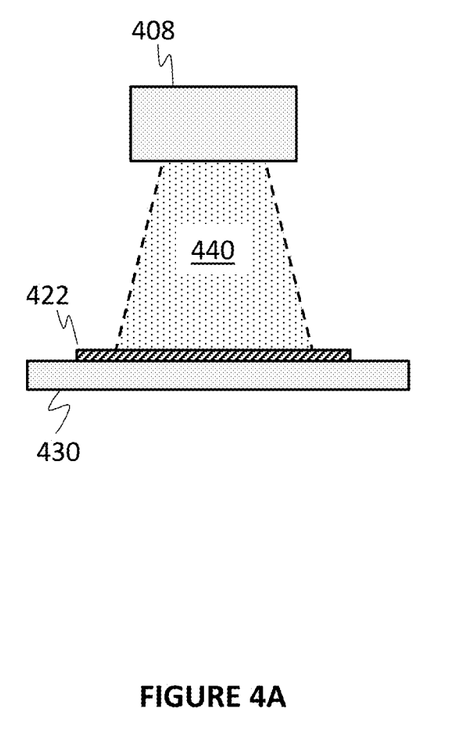
FIGS. 4A and 4B illustrate relative positions of a code reader and an object having a code imprinted thereon, according to some embodiments of the disclosure.
Figure 4B:
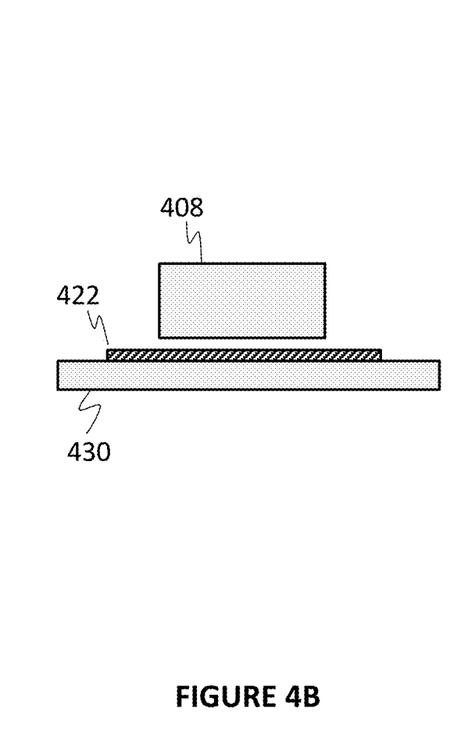

FIGS. 4A and 4B illustrate relative positions of a code reader and an object having a code imprinted thereon, according to some embodiments of the disclosure. Both FIGUREs illustrate a centroid-measuring photodetector 408, similar to the photodetector 108 described above, substantially aligned with a pattern 422, similar to the pattern 122 described above, so that sufficient portion of the pattern 422 is within a field of view of the photodetector 408, shown as a field of view 440 in FIG. 4A.

Element 430 in FIGS. 4A-4B illustrates a support layer on which the pattern 422 may be provided, e.g. a layer into which the light could be coupled and from which the light could leak out in the direction of the photodetector 408, interacting with the pattern 422 prior to being incident on the photodetector 408. This is also applicable to the object 120 and the pattern 122 described with reference to FIG. 1, although not specifically illustrated there.

FIG. 4A illustrates the photodetector 408 being provided at a greater distance from the pattern 422 than that shown in FIG. 4B. These figures illustrates that the actual distance between the pattern and the sensor(s) can vary quite a bit in different deployment scenarios, but, in each case, the methods disclosed here can provide reliable measure of the centroid.

It should be noted that an alignment error may simply be viewed as including both an error due to mechanical alignment (i.e. the second parameter above) and an error due to printer alignment (i.e. the third parameter above), since they are not easily distinguishable from one another. Both of these errors can be significantly reduced or eliminated by adopting a differential scheme in which two centroid-measuring photodetectors are used to read two different patterns imprinted on an object, such photodetectors sometimes referred to in the following as differential photodetectors. In such an embodiment, each of the two centroid-measuring photodetectors could be one of the centroid-measuring photodetectors as described above, and each of the two patterns imprinted on an object could be one of the patterns as described above. The code reader would include these two centroid-measuring photodetectors placed next to each other, with their fields of view not overlapping, so that each photodetector can read a different pattern imprinted on a given object.

Figure 5A:
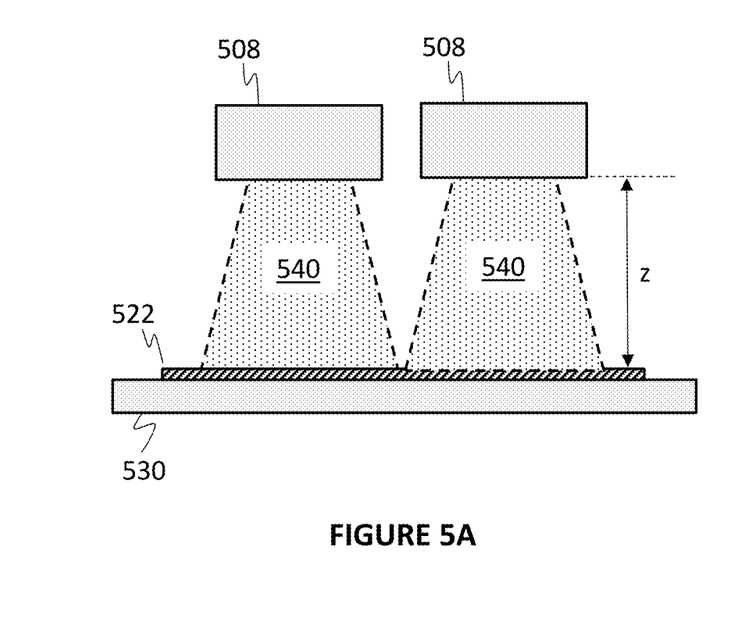
FIGS. 5A and 5B illustrate relative positions of a differential code reader and an object having a differential code imprinted thereon, according to some embodiments of the disclosure.
Figure 5B:
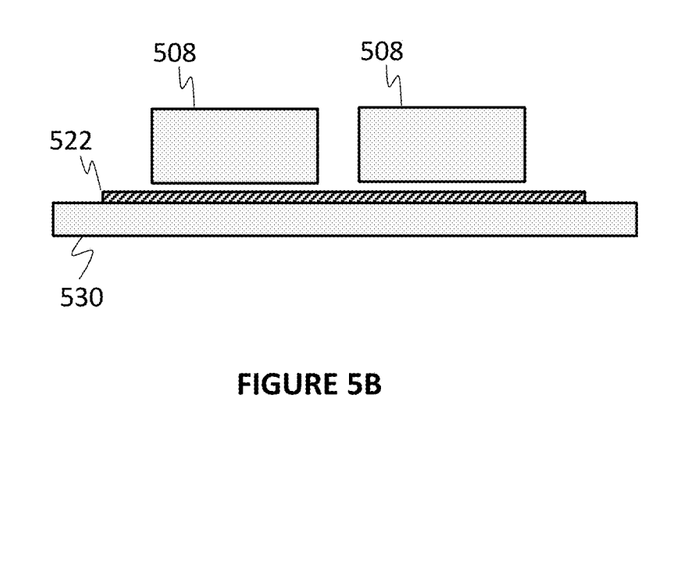

A code reader comprising differential centroid-measuring photodetectors is illustrated in FIGS. 5A and 5B which are similar to FIGS. 4A and 4B (and, therefore, all of the descriptions provided above are applicable here), except that two photodetectors 508, each having a field of view 540, are used. FIGS. 5A and 5B illustrate a single pattern 522, but that is understood that such a single pattern would include a differential pattern comprising two patterns, such as e.g. one of the three exemplary differential patterns shown in FIG. 6. Similarly, while FIG. 1 illustrates and is described with reference to a single pattern 122, descriptions provided above with respect to the code reader 102 are applicable to a code reader implementing the differential scheme described herein.

In the embodiment of the differential scheme, the two centroid-measuring photodetectors are placed at a certain known distance from one another, i.e. they are aligned. Each of the centroid-measuring photodetectors is configured to determine a centroid of a corresponding pattern. For example, the photodetector 508 shown on the left side in FIGS. 5A-5B could be configured to determine a centroid of the left pattern of one of the three differential patterns shown in FIG. 6, while the photodetector 508 shown on the right side in FIGS. 5A-5B could be configured to determine a centroid of the right pattern of one of the three differential patterns shown in FIG. 6. Thus, essentially, two pairs of coordinates are measured—a pair (x1, y1) represents a centroid of a pattern as measured by one photodetector 508, and a pair (x2, y2) represents a centroid of a pattern as measured by the other photodetector 508. The decoding logic 110 is then configured to use the difference between these two centroids, e.g. the distance (x1−x2, y1−y2) to decode data. In other words, data can be encoded into the distance between the centroids of two patterns. Such an approach eliminates any common mode alignment offsets either by relative mechanical alignment of the photodetector or by the printed pattern. In addition, by virtue of using two centroid-measuring photodetectors and differential patterns, the differential scheme allows significantly increasing the number of codes.

Optionally, additional measures may be taken in order to further reduce alignment and/or printer errors. For example, fabricating the two centroid-measuring photodetectors on the same die could allow to further reduce variations between them and to align them lithographically. This would reduce or eliminate any error in relative photodetector alignment and photodetector response. Additionally or alternatively, both patterns may be imprinted on the object using the same means, e.g. both patterns could be printed by the same printer. Any printer errors would then be cancelled out when data is decoded based on the difference between the patterns.

The distance z between the sensor and the pattern (shown e.g. in FIG. 5A) can affect the measurement of the differential centroid distance (x1−x2, y1−y2). In some embodiments, a code reader may be configured to account for this distance. To that end, a code reader may include another pair of centroid-measuring photodetectors that have overlapping fields of view and use those photodetectors to determine the distance between the photodetectors and the pattern, as described above. Such distance measurement can be used for calibrating the photodetector system. It could also enable encoding data by relative separation of the centroid-measuring photodetectors and the patterns.

Figure 7:
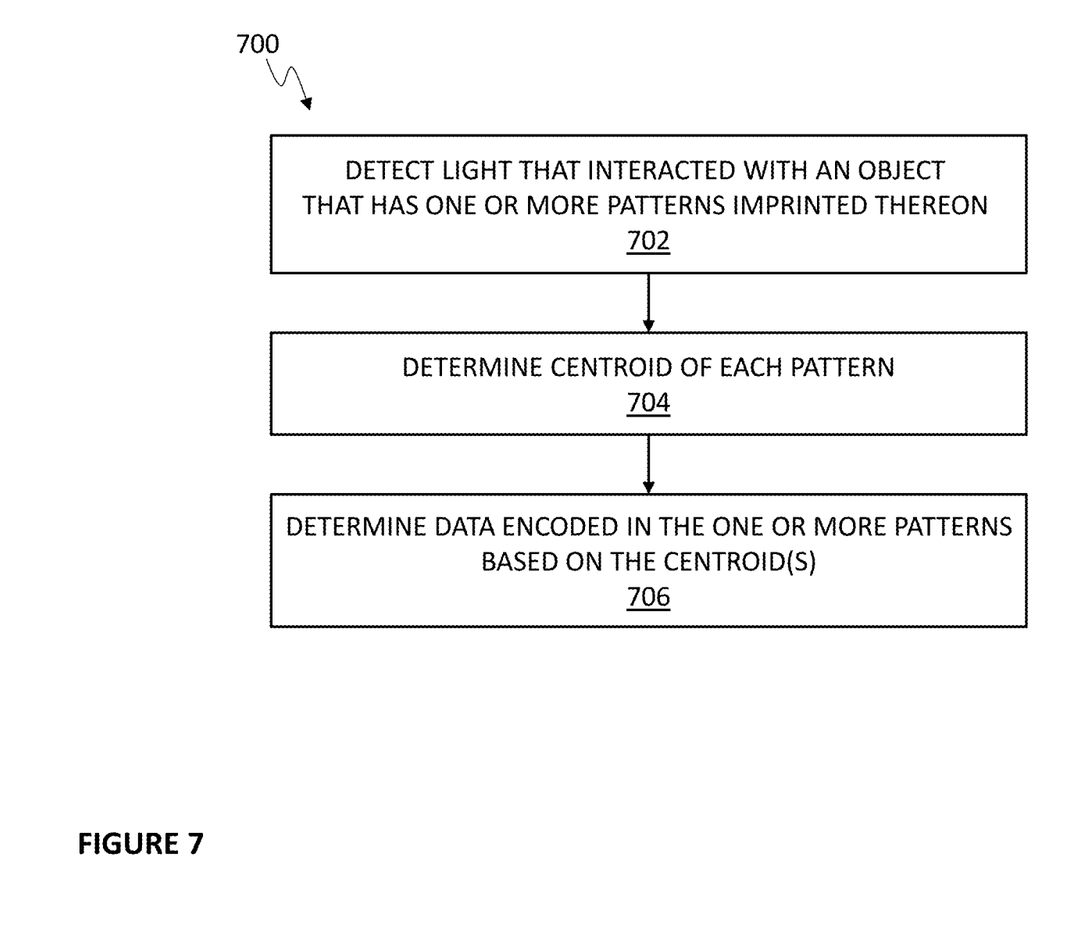
FIG. 7 illustrates a flow diagram of a code reading method, according to some embodiments of the disclosure.

FIG. 7 illustrates a flow diagram of a code reading method 700, according to some embodiments of the disclosure. Although described with reference to the systems illustrated in FIGS. 1 and 5, any systems configured to perform steps of method 700, in any order, are within the scope of the present disclosure.

At the beginning of the method, an object comprising one or more patterns imprinted thereon may be affixed to, aligned with, or inserted into a code reader. The method may begin with step 702, where one or more centroid-measuring photodetectors included within the code reader, such as e.g. photodetectors 108, 408, or 508 described above, detect light that has interacted with the one or more patterns of the object, and, in step 704, centroids of the one or more patterns are determined. In step 706, a code detection logic associated with the centroid-measuring photodetectors is configured to process the determined centroids (e.g. process coordinates indicating locations of the centroids) to determine data encoded in the one or more patterns.

SELECTED EXAMPLES

Example 1 provides a medical device assembly including a medical device reader configured to perform measurements on a medical device object, the medical device reader including a code reader, and the medical device object configured to be affixed to, aligned with, or inserted into the medical device reader and having a code provided thereon as a pattern imprinted on the object. The code reader includes one or more centroid-measuring photodetectors configured to detect light that has interacted with the pattern, where the detected light is indicative of a centroid of the pattern; and a processing logic configured to determine the centroid of the pattern from the detected light, and determine the code based on the determined centroid.

Example 2 provides the medical device assembly according to Example 1, where the medical device object includes a glucose meter strip and the medical device reader includes a glucose meter, and where the measurements performed by the medical device reader on the medical device object include measurements of one or more glucose levels based on a sample provided in the glucose meter strip.

Example 3 provides the medical device assembly according to Example 1, where the one or more centroid-measuring photodetectors include a first photodetector and a second photodetector provided at predefined positions with respect to one another (e.g. the distance between the two photodetectors is a known predefined distance), said pattern is a first pattern, the object further has a second pattern provided thereon, the first photodetector is configured to detect light that has interacted with the first pattern, where the light detected by the first photodetector is indicative of the centroid of the first pattern, the second photodetector is configured to detect light that has interacted with the second pattern, where the light detected by the second photodetector is indicative of a centroid of the second pattern, the processing logic is configured to determine the centroid of the first pattern based on light detected by the first photodetector and to determine the centroid of the second pattern based on light detected by the second photodetector, where decoding the data includes decoding the data encoded in the first and second patterns based on a distance between the centroid of the first pattern and the centroid of the second pattern.

Example 4 provides the medical device assembly according to Example 1, where each of the one or more centroid-measuring photodetectors includes a surface having an aperture; and a pair of photodetectors electrically isolated from each other at a boundary between them, the boundary aligned with the aperture.

Example 5 provides a code reading system including a first centroid-measuring photodetector configured to detect light that has interacted with a first pattern provided on an object, where the first pattern encode data and where the detected light is indicative of a centroid of the first pattern; and a processing logic configured to determine the centroid of the first pattern from the detected light, and decode the data encoded in the first pattern based on the determined centroids of the first pattern.

Example 6 provides the code reading system according to Example 5, where the first centroid-measuring photodetector includes a charge-generating region at least partially enclosed between at least a pair of charge-collecting electrodes, where: the charge-generating region is configured to generate charge as a result of the light being incident on the region, and amount of charge collected at each of the charge-collecting electrodes (e.g. the difference between the amounts of charge collected at each electrode) is indicative of the centroid of the first pattern.

Example 7 provides the code reading system according to Example 6, further including a lens configured to image the first pattern onto the first centroid-measuring photodetector.

Example 8 provides the code reading system according to Example 6, where the first centroid-measuring photodetector is in direct contact with the first pattern or are at a distance of less than 10 millimeters (i.e. in relatively close proximity with the first pattern).

Example 9 provides the code reading system according to Example 5, where the first centroid-measuring photodetector includes a surface having an aperture; and a pair of photodetectors electrically isolated from each other at a boundary between them, the boundary aligned with the aperture.

Example 10 provides the code reading system according to Example 9, where each of the pair of photodetectors is configured to generate a respective photocurrent so that the pair of photodetectors is sufficient to detect the angle of incident light, the angle of incident light being detectable based on a ratio of the photocurrents generated respectively by the pair of photodetectors, and the pair of photodetectors is aligned along an optical path without a lens, the optical path leading through the aperture and the photodetectors.

Example 11 provides the code reading system according to Example 5, where the first centroid-measuring photodetector includes a multi-pixel sensor configured to measure the centroid of the first pattern.

Example 12 provides the code reading system according to Example 5, where the code reading system further includes a second centroid-measuring photodetector provided at a predefined position with respect to the first centroid-measuring photodetector (e.g. the distance between the two photodetectors is a known predefined distance), the object further has a second pattern provided thereon, the second photodetector is configured to detect light that has interacted with the second pattern, where the light detected by the second photodetector is indicative of a centroid of the second pattern, the processing logic is further configured to determine the centroid of the second pattern based on light detected by the second photodetector, and decoding the data includes decoding the data encoded in a combination of the first and second patterns based on a distance between the centroid of the first pattern and the centroid of the second pattern.

Example 13 provides the code reading system according to Example 5, further including one or more light sources configured to generate light to interact with the first pattern provided on the object.

Example 14 provides the code reading system according to Example 13, where the one or more light sources are configured to couple the generated light into the object.

Example 15 provides the code reading system according to Example 13, where the one or more light sources are configured to illuminate the object with the generated light so that the light that has interacted with the first pattern includes a portion of the generated light that is transmitted through the first pattern.

Example 16 provides the code reading system according to Example 13, where the one or more light sources are configured to illuminate the object with the generated light so that the light that has interacted with the first pattern includes a portion of the generated light that is reflected from the first pattern.

Example 17 provides the code reading system according to Example 5, where the first pattern is a pattern of openings provided in the object.

Example 18 provides the code reading system according to Example 5, where the first pattern is a unique coding pattern.

Example 19 provides a code reading assembly including a code reader, and a coded object having a code imprinted thereon as a pattern provided on the object, where the coded object is configured to be affixed to, aligned with, or inserted into the code reader for the code reader to read the code imprinted on the coded object. The code reader includes one or more centroid-measuring photodetectors configured to detect light that has interacted with the pattern, where the detected light is indicative of a centroid of the pattern; and a processing logic configured to determine the centroid of the pattern from the detected light, and determine the code based on the determined centroid.

Variations and Implementations

It is noted that the illustrations in the FIGURES do not necessary represent true layout, orientation, sizing, and/or geometry of an actual code reader. It is envisioned by the disclosure that various suitable layouts can be designed and implemented for the code reader configured to decode data based on the centroids of patterns. Based on the descriptions provided above, a person of ordinary skill in the art can easily envision various further embodiments and configurations of encoding data into patterns and of using centroid-measuring photodetectors to read the encoded data, all of which are within the scope of the present disclosure.

FIGS. 1-7 can vary significantly to achieve equivalent or similar results, and thus should not be construed as the only possible implementation which leverages the use of context data disclosed herein.

It is envisioned that the code readers described herein and/or the associated processing modules can be provided in many areas including medical equipment, security monitoring, patient monitoring, healthcare equipment, medical equipment, automotive equipment, aerospace equipment, consumer electronics, and sports equipment, etc.

In some cases, the code reader and/or the associated processing module can be used in professional medical equipment in a healthcare setting such as doctor's offices, emergency rooms, hospitals, etc. In some cases, the code reader and/or the associated processing module can be used in less formal settings, such as schools, gyms, homes, offices, outdoors, under water, etc. The code reader and/or the associated processing module can be provided in a consumer healthcare product.

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure. For instance, instead of processing the signals in the digital domain, it is possible to provide equivalent electronics that can process the signals in the analog domain.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities. In some cases, application specific hardware can be provided with or in the processor to carry out those functionalities.

In another example embodiment, the electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the slow varying frequency tracking functionalities may be implemented in one or more silicon cores in Application Specific Integrated Circuits (ASICs), Field Programmable Gate Arrays (FPGAs), and other semiconductor chips.

Note that the activities discussed above with reference to the FIGURES are applicable to any integrated circuits that involve signal processing, particularly those that can execute specialized software programs, or algorithms, some of which may be associated with processing digitized real-time data to track a slow moving frequency. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include pulmonary monitors, heart rate monitors, pacemakers, etc. Other applications can involve automotive technologies for safety systems (e.g., stability control systems, driver assistance systems, braking systems, infotainment and interior applications of any kind). In yet other example scenarios, the teachings of the present disclosure can be applicable in the industrial markets that include process control systems aiming to track vital signs to help drive productivity, energy efficiency, and reliability.

Note that with the numerous examples provided herein, interaction may be described in terms of two, three, four, or more parts. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the features of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, parts, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to code reading illustrate only some of the possible tracking functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

What is claimed is:

1. A medical device assembly comprising:
    a medical device reader configured to perform measurements on a medical device object, the medical device reader comprising a code reader, and
    the medical device object configured to be affixed to, aligned with, or inserted into the medical device reader and having a code provided thereon as a pattern imprinted on the object,
    wherein the code reader comprises:
        one or more centroid-measuring photodetectors configured to detect light that has interacted with the pattern, wherein the detected light is indicative of a centroid of the pattern; and
        a processing logic configured to:
            determine the centroid of the pattern from the detected light, and
            determine the code based on the determined centroid.

2. The medical device assembly according to claim 1, wherein the medical device object comprises a glucose meter strip and the medical device reader comprises a glucose meter, and wherein the measurements performed by the medical device reader on the medical device object comprise measurements of one or more glucose levels based on a sample provided in the glucose meter strip.

3. The medical device assembly according to claim 1, wherein:
    the one or more centroid-measuring photodetectors comprise a first photodetector and a second photodetector provided at predefined positions with respect to one another,
    said pattern is a first pattern,
    the object further has a second pattern provided thereon,
    the first photodetector is configured to detect light that has interacted with the first pattern, wherein the light detected by the first photodetector is indicative of the centroid of the first pattern,
    the second photodetector is configured to detect light that has interacted with the second pattern, wherein the light detected by the second photodetector is indicative of a centroid of the second pattern,
    the processing logic is configured to determine the centroid of the first pattern based on light detected by the first photodetector and to determine the centroid of the second pattern based on light detected by the second photodetector,
    wherein determining the code comprises determining the code encoded in the first and second patterns based on a distance between the centroid of the first pattern and the centroid of the second pattern.

4. The medical device assembly according to claim 1, wherein each of the one or more centroid-measuring photodetectors comprises:
    a surface having an aperture; and
    a pair of photodetectors electrically isolated from each other at a boundary between them, the boundary aligned with the aperture.

5. The medical device assembly according to claim 4, wherein:
    each of the pair of photodetectors is configured to generate a respective photocurrent,
    the pair of photodetectors is aligned along an optical path without a lens, the optical path leading through the aperture and the photodetectors, and
    the processing logic is configured to determine the centroid of the pattern based on a ratio of the photocurrents generated by the pair of photodetectors.

6. The medical device assembly according to claim 1, wherein:
    the one or more centroid-measuring photodetectors comprise a charge-generating region at least partially enclosed between at least a pair of charge-collecting electrodes,
    the charge-generating region is configured to generate charge as a result of the light being incident on the region, and
    an amount of charge collected at each of the charge-collecting electrodes is indicative of the centroid of the pattern.

7. The medical device assembly according to claim 6, further comprising a lens configured to image the pattern onto the one or more centroid-measuring photodetectors.

8. The medical device assembly according to claim 6, wherein the one or more centroid-measuring photodetectors are in direct contact with the pattern or are at a distance of less than 10 millimeters from the pattern.

9. The medical device assembly according to claim 1, wherein the one or more centroid-measuring photodetectors comprise a multi-pixel sensor configured to measure the centroid of the pattern.

10. The medical device assembly according to claim 1, further comprising one or more light sources configured to generate light to interact with the pattern provided on the medical device object.

11. The medical device assembly according to claim 10, wherein the one or more light sources are configured to couple the generated light into the medical device object.

12. The medical device assembly according to claim 10, wherein the one or more light sources are configured to illuminate the medical device object with the generated light so that the light that has interacted with the pattern comprises a portion of the generated light that is transmitted through the pattern.

13. The medical device assembly according to claim 10, wherein the one or more light sources are configured to illuminate the object with the generated light so that the light that has interacted with the pattern comprises a portion of the generated light that is reflected from the pattern.

14. The medical device assembly according to claim 1, wherein the pattern is a pattern of openings provided in the medical device object.

15. The medical device assembly according to claim 1, wherein the pattern is a unique coding pattern.

16. A method for reading a code provided as a pattern imprinted on a medical device object, the method comprising:
- receiving measurements from one or more centroid-measuring photodetectors of a medical device reader, the one or more centroid-measuring photodetectors configured to measure light that has interacted with the pattern when the medical device object is affixed to, aligned with, or inserted into the medical device reader;
- determining the centroid of the pattern based on the measurements; and
- determining the code based on the determined centroid.

17. The method according to claim 16, wherein each of the one or more centroid-measuring photodetectors comprises:
- a surface having an aperture; and
- a pair of photodetectors electrically isolated from each other at a boundary between them, the boundary aligned with the aperture.

18. The method according to claim 16, wherein each of the one or more centroid-measuring photodetectors comprises a charge-generating region at least partially enclosed between at least a pair of charge-collecting electrodes, where the charge-generating region is configured to generate charge as a result of the light being incident on the region, and amount of charge collected at each of the charge-collecting electrodes is indicative of the centroid of the pattern.

19. The method according to claim 16, wherein each of the one or more centroid-measuring photodetectors comprises a multi-pixel sensor.

20. A system for reading a code provided as a pattern imprinted on a medical device object, the system comprising:
- means for receiving measurements from one or more centroid-measuring photodetectors of a medical device reader, the one or more centroid-measuring photodetectors configured to measure light that has interacted with the pattern when the medical device object is affixed to, aligned with, or inserted into the medical device reader;
- means for determining the centroid of the pattern based on the measurements; and
- means for determining the code based on the determined centroid.

* * * * *